(12) United States Patent
Bao et al.

(10) Patent No.: US 6,721,691 B2
(45) Date of Patent: Apr. 13, 2004

(54) METROLOGY HARDWARE SPECIFICATION USING A HARDWARE SIMULATOR

(75) Inventors: Junwei Bao, Fremont, CA (US); Nickhil Jakatdar, Los Altos, CA (US)

(73) Assignee: Timbre Technologies, Inc., Santa Clara, CA (US)

(*) Notice: Subject to any disclaimer, the term of this patent is extended or adjusted under 35 U.S.C. 154(b) by 0 days.

(21) Appl. No.: 10/108,818

(22) Filed: Mar. 26, 2002

(65) Prior Publication Data
US 2003/0187602 A1 Oct. 2, 2003

(51) Int. Cl.[7] ........................... G01B 11/24; G06F 15/00
(52) U.S. Cl. ..................... 702/189; 356/601; 356/369; 438/16; 702/32; 702/81; 702/83; 702/84
(58) Field of Search ........................... 702/83, 84, 32, 702/81, 90, 94, 189; 355/77; 356/237.2, 354, 355, 356, 363, 384, 400, 401, 601; 438/14, 16; 716/19

(56) References Cited

U.S. PATENT DOCUMENTS

| | | | |
|---|---|---|---|
| 5,164,790 A | 11/1992 | McNeil et al. | 356/496 |
| 5,655,110 A | 8/1997 | Krivokapic et al. | 716/19 |
| 6,449,031 B1 | 9/2002 | Grodnensky et al. | 355/77 |
| 6,458,610 B1 * | 10/2002 | Lensing et al. | 438/16 |
| 2002/0018217 A1 | 2/2002 | Weber-Grabau et al. | 356/601 |
| 2002/0113966 A1 | 8/2002 | Shchegrov et al. | 356/369 |

OTHER PUBLICATIONS

Niu et al., "Caching of intra–layer calculations for rapid rigorous coupled–wave analyses", PubNo: US 2002/0033954 A1, PubDate: Mar. 21, 2202, FiledDate: Jan. 25, 2001.*

Shchegrov et al., "Parametric profiling using optical spectroscopic systems", PubNo: US 2002/0113966 A1, PubDate: Aug. 22, 2003, FiledDate: Dec. 19, 2000.*

* cited by examiner

Primary Examiner—John Barlow
Assistant Examiner—John Le
(74) Attorney, Agent, or Firm—Morrison & Foerster LLP

(57) ABSTRACT

A method and system in metrology for integrated circuits, for incorporating the effects of small metrology hardware-based and material-based parameter variations into a library of simulated diffraction spectra. In a first embodiment, a method is disclosed for determining metrology hardware specification ranges that correspond to specified CD measurement accuracy. In a second embodiment, a method for modifying a library of simulated diffraction spectra for optimization to the particular parameters of a specific piece of metrology hardware and specific material batches is disclosed.

27 Claims, 8 Drawing Sheets

METROLOGY HARDWARE SPECIFICATION USING A HARDWARE SIMULATOR

CROSS-REFERENCE TO RELATED APPLICATIONS

This application relates to co-pending U.S. patent application Ser. No. 09/764,780 entitled "Caching of Intra-Layer Calculations for Rapid Rigorous Coupled-Wave Analyses" by Niu, et al., filed on Jan. 25, 2001; co-pending US Patent Application (number to be assigned) by Junwei Bao, et al., entitled "Profile Refinement for Integrated Circuit Metrology", filed with the USPTO on Feb. 12, 2002 all owned by the assignee of this application and incorporated herein by reference.

FIELD OF THE INVENTION

The present invention relates to metrology for semiconductor manufacturing a applications, and in particular to a method and system for reducing measurement inaccuracies.

BACKGROUND OF THE INVENTION

As integrated circuits evolve towards smaller critical dimensions (CD's) and faster response time, new challenges are encountered in the manufacturing processes. Accurate metrology for measurement of features with sizes on the order of 100 nm or smaller is desirable.

Optical metrology has emerged as an effective tool, with several advantages over other metrology methods such as Scanning Electron Microscopy (SEM). Optical probes are non-destructive, can be employed in production monitoring and control, and can be used for determination of thickness and topographic information as well as for CD measurement.

In a method for optical metrology known as Optical Digital Profilometry (ODP), scatterometry is used to reconstruct a diffraction grating profile from its optical diffraction responses, at a fixed incident angle and multiple wavelengths. A library-based methodology for profile extraction is provided, whereby libraries of spectral responses are created for simulated grating profiles which include such detailed profile characteristics as: rounding, footing, T-topping, material thickness variation, sidewall angles, and CD variation. Mask information, thin-film information such as parameters describing optical properties n & k, and thickness values, are inputs that are used to compute the diffraction signal, which may be a spectral scattering response signal, of a collection of simulated profiles. To determine the profile of a sample, e.g. an integrated circuit, having periodic structures, the spectral scattering response is measured for that sample. The measured spectral scattering response from the sample is compared with the library of simulated spectral scattering responses, and a best match is found, i.e., a profile whose simulated diffraction signals best match the actual measured diffraction signals.

The simulated spectral scattering responses are typically calculated by a grating response simulator which utilizes Rigorous Coupled-Wave Analysis (RCWA) analytical techniques, as described in the article by Niu et al. Other simulation algorithms may also be used to calculate the spectral scattering responses. An integral method is described in "*Numerical Methods for the Analysis of Scattering from Nonplanar Periodic Structures,*", A. R. Neureuther and K Zaki, Int'l URSI Symposium on Electromagnetic Waves, Stresa, Italy, pp 282–285, 1969. A differential method is described in "*Systematic Study of Resonances Holographic Thin Film Coulers*", M Neviere et al, Optics Communications, Vol. 9, No. 1, pp 48–53, September 1973.

The hardware used in conjunction with metrology, which may include a metrology beam source, ellipsometer, and reflectometer, is subject to parameters that are not exactly reproducible. Examples of metrology hardware-related variable parameters include: angle of metrology beam incidence, numerical aperture, wavelength range, polarization, and noise. These metrology hardware parameters may display time variation (within a specification range) for a single piece of metrology hardware, and they may also vary between pieces of metrology hardware of the same type.

In addition to the variability of metrology hardware-related parameters, material-based parameters, e.g., optical characteristics n and k, may vary from sample batch to batch (as in different semiconductor wafer batches) or across a single batch of material (as in wafer-to-wafer variations).

The variation in metrology hardware and material parameters has caused problems relating to metrology. The user determined accuracy requirements from metrology systems are generally based on the measurement accuracy, e.g., accuracy of measured CD's. However, the accuracy of metrology hardware is based on hardware specification ranges, i.e., the variability of hardware parameters. The relationship between the metrology hardware specification ranges and the associated measurement accuracy is not generally available for the hardware designer and the user.

A second problem occurs in library-based metrology systems. The library diffraction signals are calculated according to inputs based on a particular set of hardware specifications, and according to ideal material characteristics. If the actual pieces of hardware and batch of material used in the measurement of a sample's diffraction signal have slightly different specifications or characteristics than those used in the library calculations, inaccuracies are incurred when matching the measured diffraction signal to the calculated library diffraction signals.

SUMMARY OF THE INVENTION

The method in accordance with embodiments of the present invention relates to a method and system for incorporating the effects of metrology hardware and material variations into a calculated diffraction signal library used in metrology, optical metrology being one example.

In a first embodiment, a method is disclosed for determining metrology hardware specification ranges that correspond to acceptable CD measurement accuracy. In this method, simulated diffraction spectra are calculated corresponding to varying metrology hardware parameters within hardware specification ranges. These spectra may be calculated using a grating response simulator. The correspondences between changes in metrology hardware parameters and changes in CD measurements are determined by comparisons with library spectra. Acceptable metrology hardware specification ranges are then linked to acceptable CD measurement accuracy. The correspondence may be utilized in two ways: either by specifying desired measurement accuracy and calculating necessary metrology hardware specification ranges to provide that accuracy, or by calculating measurement accuracy resulting from given metrology hardware specification ranges.

In a second embodiment, a method for modifying a library diffraction spectrum so as to be optimized to the particular parameters of a specific piece of metrology hardware and specific material batches is disclosed. A parameter modification vector, which describes the differences between the actual measurement parameters and the parameters used in calculating the library spectra, is determined from metrology hardware specifications and material properties for the particular system and material in use. This parameter modification vector is used to calculate the corresponding modification to the library diffraction spectrum. A modified library can then be created, which is used to more accurately profile samples using the specific material batch and the specific metrology hardware.

DETAILED DESCRIPTION OF THE INVENTION

The present invention provides a method for accounting for material-based or hardware-based parameter variations while still maintaining a specified degree of accuracy in metrology measurements, optical metrology measurements being one example. A method for calculating diffraction spectra used in optical metrology is described in copending U.S. patent application Ser. No. 09/764,780 entitled "Caching Of Intra-Layer Calculations For Rapid Rigorous Coupled-Wave Analyses", by Niu et al, filed Jan. 25, 2001, which is hereby incorporated by reference.

Figure 1:
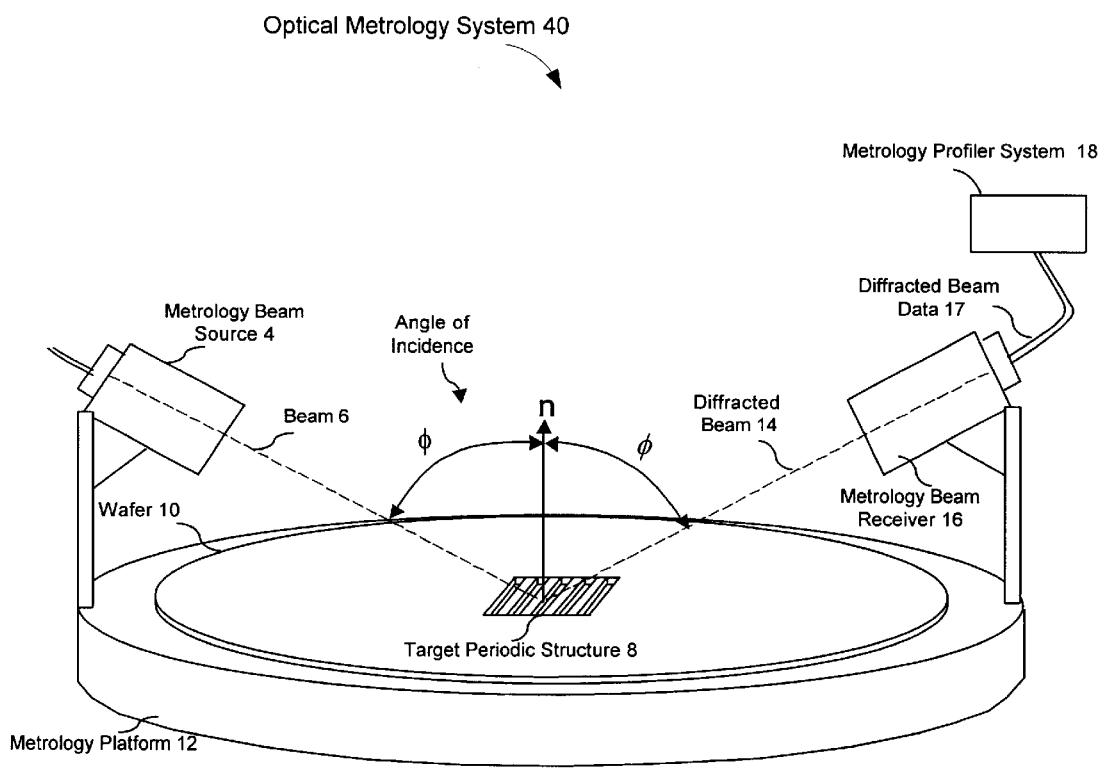
FIG. 1 illustrates a metrology system used to measure the diffracted spectra from integrated circuit periodic structures.

FIG. 1 illustrates a typical optical metrology system configuration. Metrology system 2 comprises a metrology beam source 4 projecting a beam 6 at the target sample periodic structure 8, which may be in a wafer 10 mounted on a platform 12. Beam 6 is directed at angle of incidence $\phi$ from the normal towards periodic structure 8. The diffracted beam 14 is received and measured by beam receiver 16. The measured diffracted beam spectral data 17 is provided to a metrology profiler system 18, generally a computerized system, which compares the measured diffracted beam data 17 with a library of calculated diffracted beam spectra representing varying combinations of structural profiles.

A first embodiment of the invention discloses a method for determining metrology hardware specification ranges that correspond to desired accuracy specifications in measurement results.

A second embodiment of the present invention provides a method for modifying a library of diffraction spectra, which was calculated based on the "ideal" specifications of a particular piece of metrology hardware, so as to be usable on another equivalent piece of metrology hardware having slightly different actual specifications, and additionally to be usable with different batches of sample materials having slightly different material characteristics.

Figure 2:
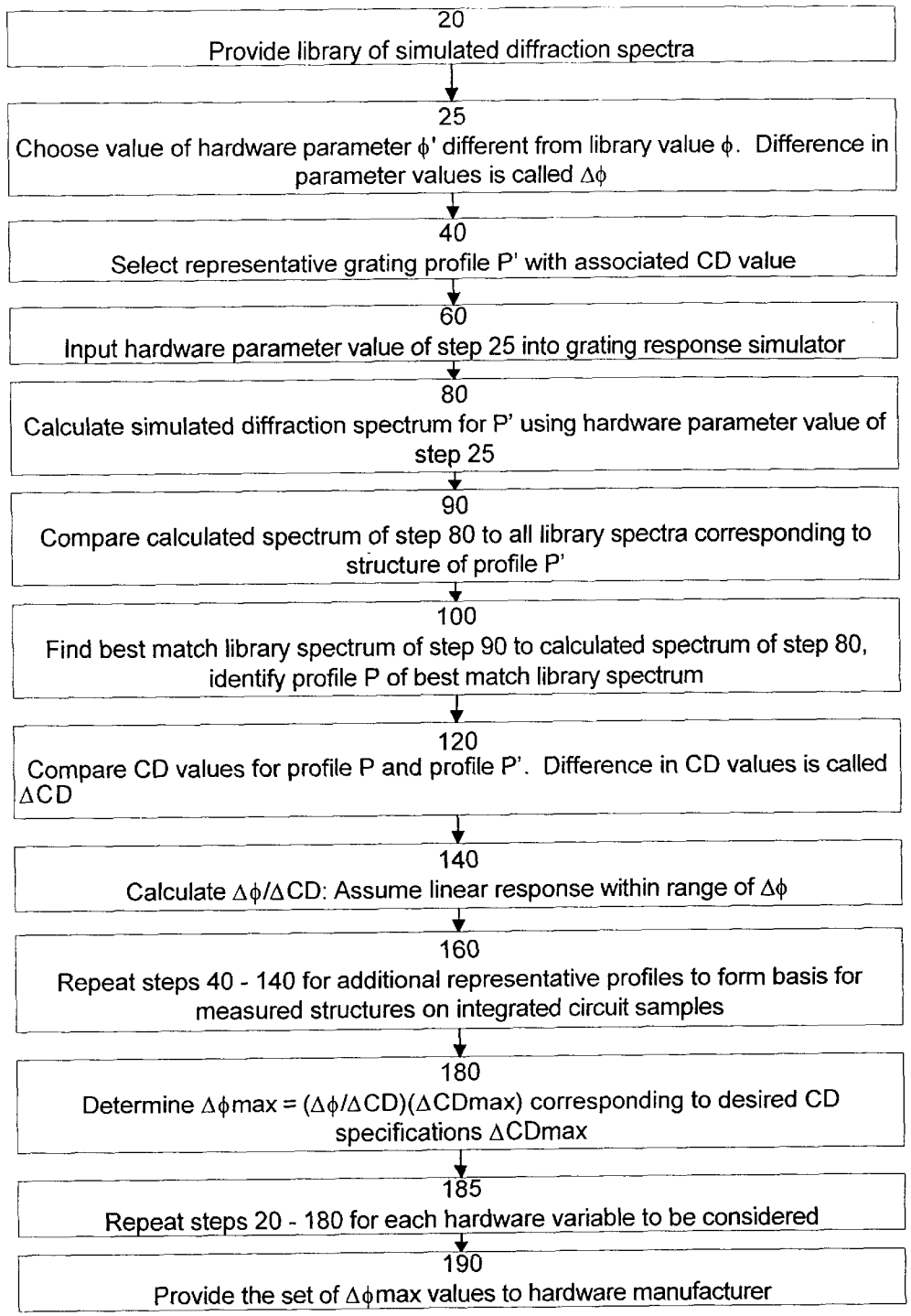
FIG. 2 is a flow chart outlining steps for determining the correspondence between metrology hardware specifications and measurement accuracy.

FIG. 2 is a flow chart describing the method for the first embodiment of the invention. By way of example, the metrology hardware-based parameter used to illustrate the method is chosen to be angle of incidence of the metrology beam onto the sample. The same steps are repeated for each metrology hardware-based parameter expected to have a significant effect on measurement accuracy. Such metrology hardware parameters may include numerical aperture, polarization, and azimuthal angle of incidence with respect to the grating direction.

In Step 20, provide a library of simulated diffraction spectra, hereinafter interchangeably referred to as spectral scattering response functions, for representative grating profiles. The library spectra are calculated using a set of input parameters that include metrology hardware parameters and materials parameters. The input parameters used in the library calculations are set at the "ideal" values corresponding to the preferred metrology hardware specifications for the equipment used in the metrology system, and to ideal material properties of the samples to be profiled.

The set of profiles chosen to form the library may be determined so as to provide a specified maximum extent of non-linearity between data points. A method for determining the density of library data points necessary in order to ensure a specified maximum extent of non-linearity is described in the co-pending U.S. Patent Application (number to be assigned) by Junwei Bao, et al., entitled "*Profile Refinement for Integrated Circuit Metrology*", filed with the USPTO on Feb. 12, 2002, which is hereby incorporated in its entirety by reference. A library created according to this method will hereinafter be referred to as a refined resolution library.

In Step 25, choose an angle of incidence $\phi'$ of incoming beam 6 onto sample surface 8, which is different from the library value of angle of incidence $\phi$ used to calculate simulated spectra in the library. By way of example, if the library value of angle of incidence $\phi$ were 45 degrees, then angle of incidence $\phi'$ might be chosen to be 46 degrees. The difference in angle of incidence between $\phi$ and $\phi'$ is termed $\Delta\phi$.

Figure 3A:
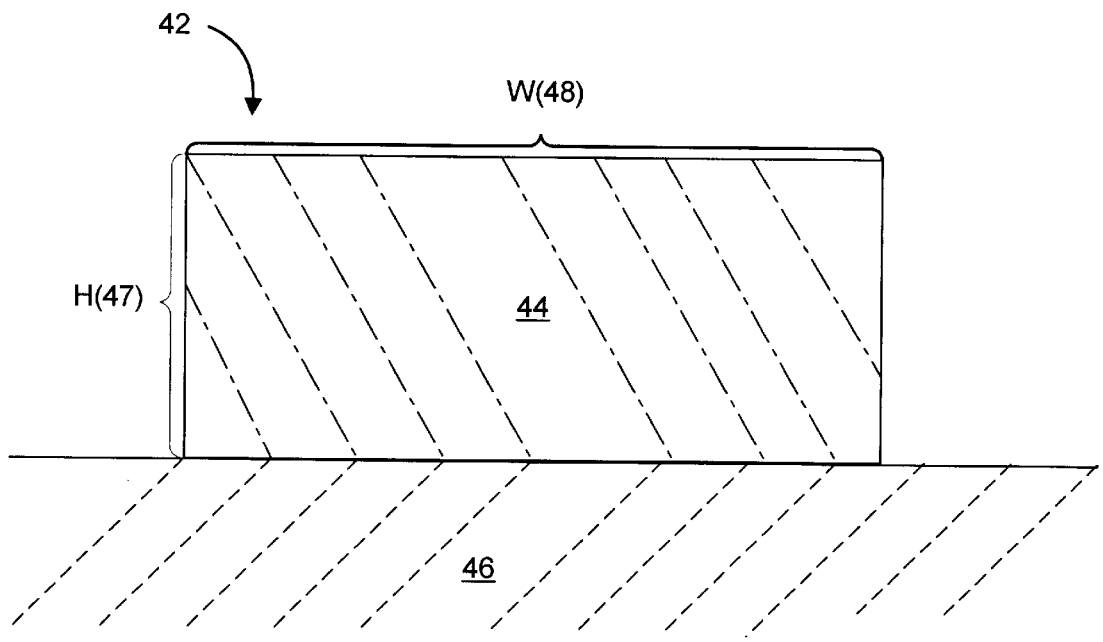
FIG. 3a shows an exemplary structural profile used to illustrate the method described in FIG. 2.

In Step 40, choose a representative grating profile P' having a structure and CD's. CD's can be defined as various profile parameters, and may include absolute width measurements, top and bottom width measurements, percentage amount of rounding or topping, or other user-defined parameters. A complete set of representative, or "building-block" profiles, forms a substantially complete basis for the actual structures to be measured on samples such as integrated circuits. For example, as illustrated in FIG. 3a, profile P'(42) might be chosen to have a structure that includes a polysilicon line (44) atop silicon dioxide (46), having height H (47) and bottom width (corresponding to the CD) of W (48).

In Step 60, provide the angle of beam incidence $\phi$ chosen in Step 25 as an input value for the grating response simulator.

In Step 80, calculate an output diffraction spectrum from the profile P' using the structure of Step 40 and the angle of beam incidence $\phi'$ of Step 25.

In Step 90, compare the calculated output diffraction spectrum for profile P' with the calculated library spectra corresponding to the structure of Step 40.

In Step 100, find the best match of the library spectra of Step 90 to the calculated spectrum of Step 80 from profile P'. Identify the profile P of the best match library spectrum.

In Step 120, compare CD's for the library profile P and profile P'. The absolute difference in CD's is termed ΔCD.

In Step 140, calculate Δϕ/ΔCD. Assume that the metrology hardware specification is sufficiently tight to yield a linear response of Δϕ/ΔCD within the range of Δϕ. This assumption is generally valid, since metrology hardware specification ranges are usually quite small, e.g., 2 to 3 degrees for angle of incidence. In general, the range of parameter variation that yields a linear response is up to approximately 10%.

In Step 160, repeat steps 40–140 for a sufficient number of other representative profiles to form a substantially complete basis for the actual structures to be measured on samples such as integrated circuits. A typical set of building-block profiles for the aforementioned polysilicon line on oxide might comprise a rectangle, a trapezoid, with the possible inclusion of top rounding and/or undercut at the bottom. Other processing structures might also include a stack of rectangles or trapezoids. If the Δϕ/ΔCD values differ between profiles, choose the smallest value of Δϕ/ΔCD to use in the calculation of step 180. This corresponds to the largest CD variation for a given variation of angle of incidence.

In Step 180, determine $\Delta\phi_{max}$ corresponding to desired CD specifications $\Delta CD_{max}$ according to:

$$\Delta\phi_{max} = \frac{\Delta\phi}{\Delta CD}(\Delta CD_{max}).$$

In Step 185, if more than one metrology hardware parameter is variable, Steps 20–180 are repeated for each variable metrology hardware parameter to be considered. In this case, the overall CD variation is calculated taking into account all the parameter variations. The approximation is made that the CD variations caused by multiple metrology hardware parameter variations are directly additive, i.e., $$\Delta CD_{max} = \Sigma(\Delta CD_{param1} + \Delta CD_{param2} + \ldots),$$

where $\Delta CD_{param1}$ is the CD variation caused by the variation of parameter 1, etc. The metrology hardware designer and/or the metrology engineer must determine how much CD error is to be allocated to each of the parameter variations, and design the metrology hardware specifications accordingly.

Figure 3B:
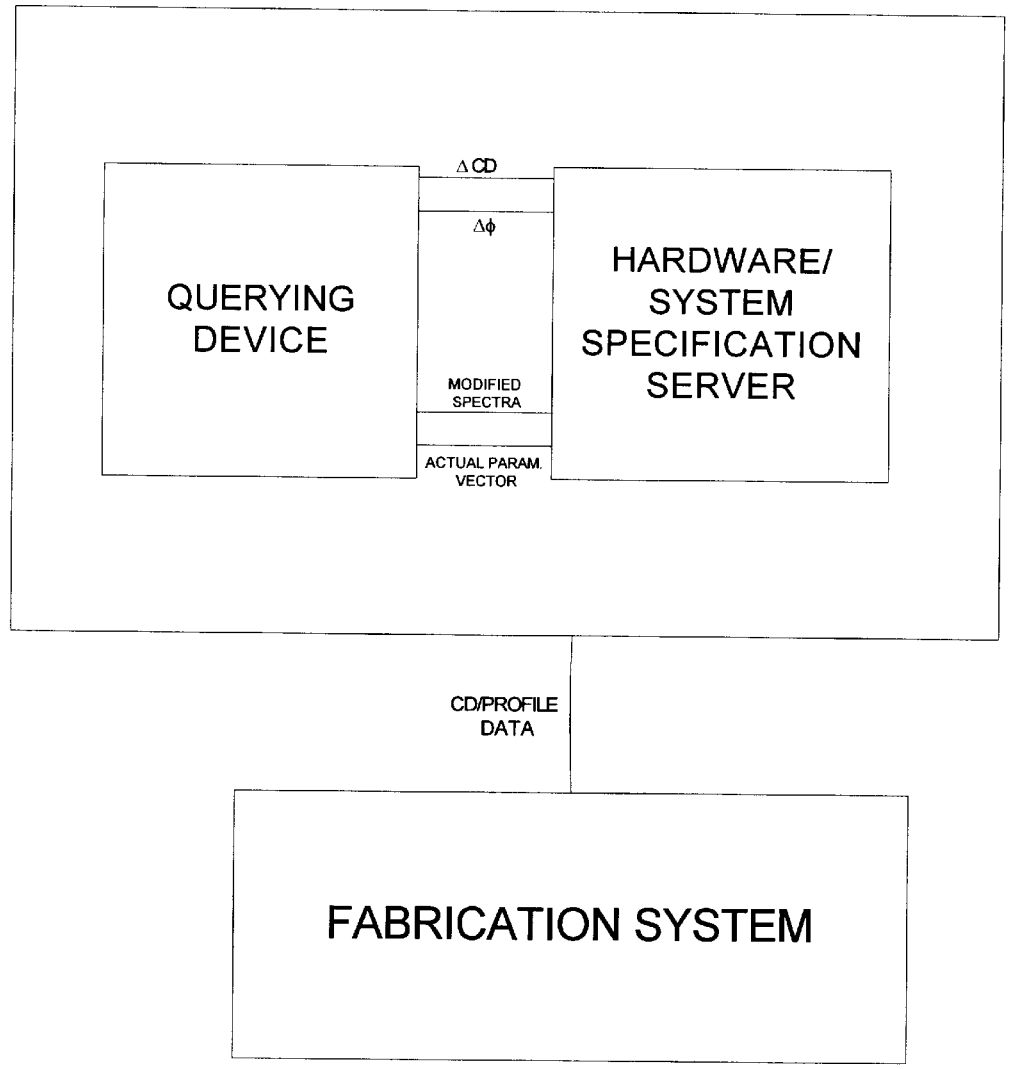
FIG. 3b shows a block diagram of a metrology hardware/specification server coupled to a fabrication system.

Referring to FIG. 3b, in the ideal case, this embodiment could be implemented and resulting data stored in a database; tables of values for metrology hardware parameter variation and the corresponding variation in CD could be stored in a metrology hardware/system specification server 186, and accessed via a querying device 187. The server and inquiry device could be integrated into a fabrication system 188 such as a lithography or etch system, providing CD/profile data. FIG. 3b shows a block diagram of such a system. The values of (Δϕ/ΔCD) as well as corresponding ratios for other metrology hardware variables could be determined and stored for all the building block process structures of Step 160. The data could be provided as standard information to the metrology hardware designer for use in designing a metrology system. User-specified values for $\Delta CD_{max}$ would determine necessary specification ranges for the metrology hardware.

In Step 190, the set of $$\Delta\phi_{max} = \frac{\Delta\phi}{\Delta CD}(\Delta CD_{max})$$

values is provided to the metrology hardware manufacturer to be implemented into metrology hardware specifications.

An alternative sub-embodiment utilizes the same method to determine resulting CD accuracy when the metrology hardware specification values are given.

A second embodiment of the present invention provides a method for modifying a library of diffraction spectra, which was calculated based on the "ideal" specifications of a particular piece of metrology hardware, so as to be usable on another equivalent piece of metrology hardware having slightly different actual specifications, and additionally to be usable with different batches of sample materials having slightly different material characteristics. The assumption is made that variations between different pieces of metrology hardware and different material batches are small. The changes in diffraction spectra are approximated to be linear with respect to the parameter change within that range and within that portion of the library.

Figure 4:
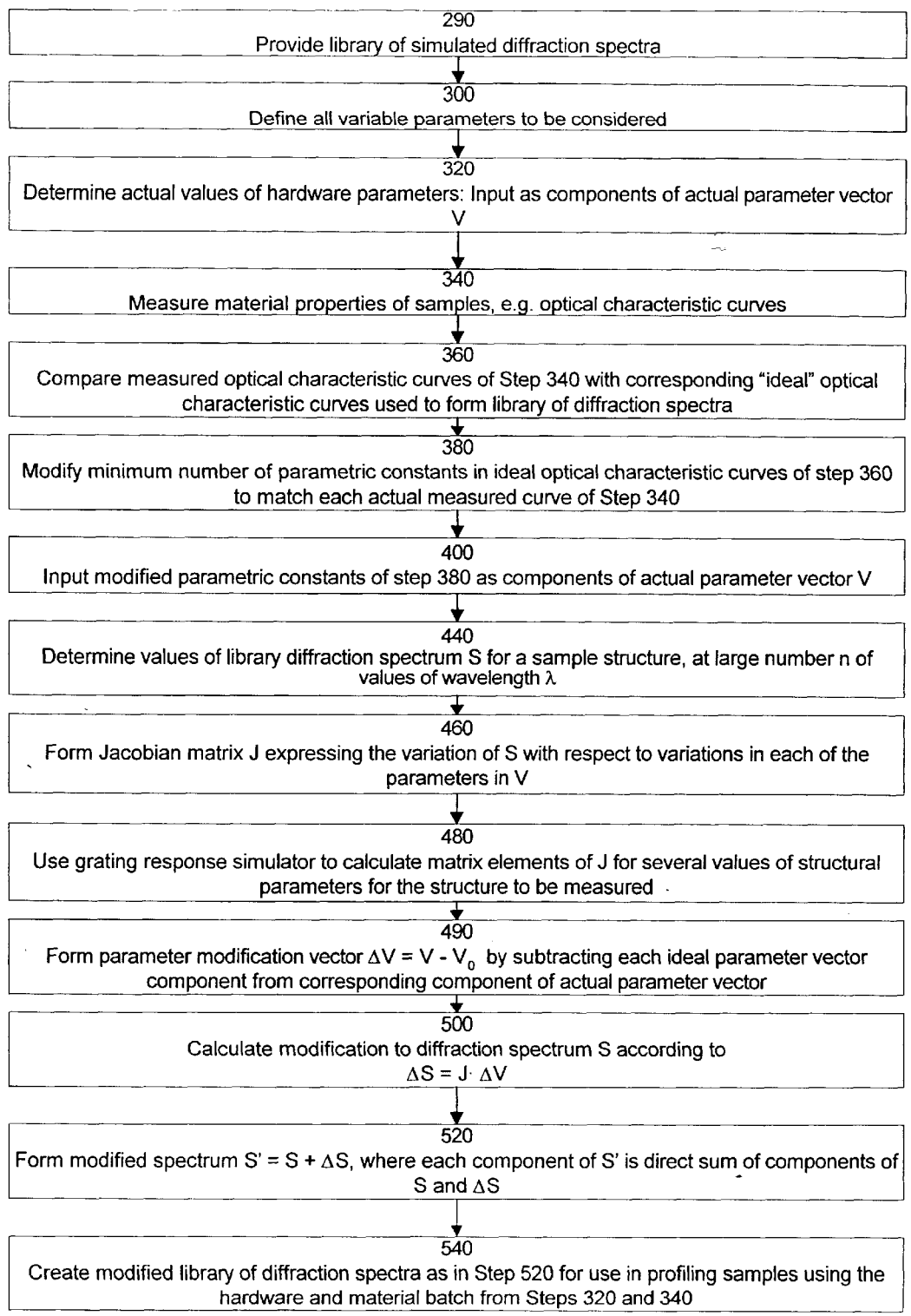
FIG. 4 is a flow chart outlining steps for modifying a library diffraction spectrum so as to customize it for the particular piece of metrology hardware and batch of material being used.

FIG. 4 is a flow chart of the second embodiment.

In Step 290, provide a library of simulated diffraction spectra for representative grating profiles. The library spectra are calculated using a set of input parameters that include metrology hardware parameters and materials parameters. The input parameters used in the library calculations are set at the "ideal" values corresponding to the preferred metrology hardware specifications for the equipment used in the metrology system, and to ideal material properties of the samples to be profiled. The library may be created according to the linearity criteria described in the aforementioned co-pending U.S. Patent Application by Junwei Bao, et al., entitled "Profile Refinement for Integrated Circuit Metrology".

In Step 300, the variable parameters to be considered are defined. These may include optical material-related parameters such as those used to describe material properties (e.g., optical characteristics n and k), sample surface roughness, and metrology hardware-related parameters such as numerical aperture, angle of incidence, resolution, polarization, and azimuthal angle of incidence with respect to the grating direction. Each of these parameters are inputs used by a grating response simulator (which may, by way of example, be as described in the above-referenced article by Niu et al), to calculate the diffraction spectrum, i.e., spectral scattering response function S. Input parameters are not limited to those referred to in the article by Niu.

In Step 320, determine actual values of metrology hardware parameters for the particular piece of metrology hardware to be used, according to the manufacturer specifications. Provide these metrology hardware parameters as components of an actual parameter vector V.

In Step 340, measure all material properties of the samples to be profiled, such as optical characteristics defined in Step 300, as a function of wavelength λ across the wavelength range used in the optical metrology measurements. By way of example, n vs λ and k vs λ curves are measured for the particular batch of material to be profiled.

In Step 360, compare the measured optical-characteristic curves of Step 340 with corresponding "ideal" optical-characteristic curves from which the library of diffraction spectra is formed. The ideal optical-characteristic curves can be expressed in parametric equation forms, which are known in the art and which generally contain parametric constants.

By way of example, one form of an optical-characteristic equation for index of refraction n is a Cauchy equation wherein n is expressed as:

$$n(\lambda)=K_0+K_2/\lambda^2+K_4/\lambda^4$$

where $K_0$, $K_2$, $K_4$ are parametric constants.

A similar equation can be formed for the extinction coefficient k wherein k is expressed as:

$$k(\lambda)=K_1/\lambda+K_3/\lambda^3+K_5/\lambda^5.$$

In this case, the ideal index of refraction curve used in the formation of the library of diffraction spectra is obtained from the ideal optical-characteristic equation $$n_0(\lambda)=K_{00}+K_{20}/\lambda^2+K_{40}/\lambda^4$$

where $K_{00}$, $K_{20}$, $K_{40}$ are the ideal parametric constants which vary from material to material and which are used as inputs to compute the library, i.e., the diffraction responses of a collection of simulated profiles.

In Step 380, modify the fewest possible number of parametric constants or functions $K_n$ in each ideal optical-characteristic equation of Step 360 in order to match the optical-characteristic curves to the actual measured curves of Step 340. For example, if the ideal n vs $\lambda$ curve can be sufficiently matched to the actual measured n vs $\lambda$ curve by modifying only $K_0$ and $K_2$, then only those two inputs to the library need be considered as parametric inputs relating to n, according to Step 300. The degree of match considered sufficient is user-determined. The modified K's are the actual rather than ideal parametric values for the particular material batch. Methods for extracting parameter values from measured curves for materials characteristics such as n and k are known in the art. An example of such methods is found in *"An Integrated System of Optical Metrology for Deep Sub-Micron Lithography"*, Xinhui Niu, PhD Thesis, Memorandum No. UCB/ERL M99/27, 1999, University of California at Berkeley, Chapters 3 and 4.

In Step 400, include all modified parametric constants or functions of Step 380 as further components of the actual parameter vector V of Step 320. By way of example, if only angle of incidence (AOI), numerical aperture (NA), and index of refraction parametric constants $K_0$ and $K_2$ were parameters, which varied between materials batches and between pieces of metrology hardware, the actual parameter vector could be written as $$V=(AOI, NA, K_0, K_2).$$

In general, more components to the actual parameter vector would be considered. The $j^{th\ parameter}$ in the parameter vector is called $p_j$: in the aforementioned example, AOI is $p_1$, NA is $p_2$, $K_0$ is $p_3$, and $K_2$ is $p_4$.

In Step 440, determine values of a library diffraction spectrum, i.e., spectral scattering response function S (which has been calculated by the grating response simulator) for a sample structure (which may correspond to a library building-block structure, or may correspond to an actual structure to be measured) at a large number n of values of wavelength $\lambda$, with n generally equal to 50, across the range of $\lambda$ used. S then has n components, denoted as $$S_1=S(\lambda_1), \ldots S_n=S(\lambda_n).$$

In Step 460, form a Jacobian matrix J expressing the variation of S with respect to variations in V, i.e., variations in any or all of the parameters in the parameter vector V. For example, if V were that of the example of Step 400, the Jacobian matrix would be of the form:

$$J = \partial S/\partial V = \begin{pmatrix} \dfrac{\partial S_1}{\partial(AOI)} & \dfrac{\partial S_1}{\partial(NA)} & \dfrac{\partial S_1}{\partial K_0} & \dfrac{\partial S_1}{\partial K_2} \\ \dfrac{\partial S_2}{\partial(AOI)} & \dfrac{\partial S_2}{\partial(NA)} & \dfrac{\partial S_2}{\partial K_0} & \dfrac{\partial S_2}{\partial K_2} \\ \vdots & & & \\ \dfrac{\partial S_n}{\partial(AOI)} & \dfrac{\partial S_n}{\partial(NA)} & \dfrac{\partial S_n}{\partial K_0} & \dfrac{\partial S_n}{\partial K_2} \end{pmatrix}$$

where $$\frac{\partial S_i}{\partial p_j}$$

is the partial derivative of the $i^{th}$ component of S, i.e., the value of S at wavelength X value i, with respect to parameter $p_j$.

Figure 5:
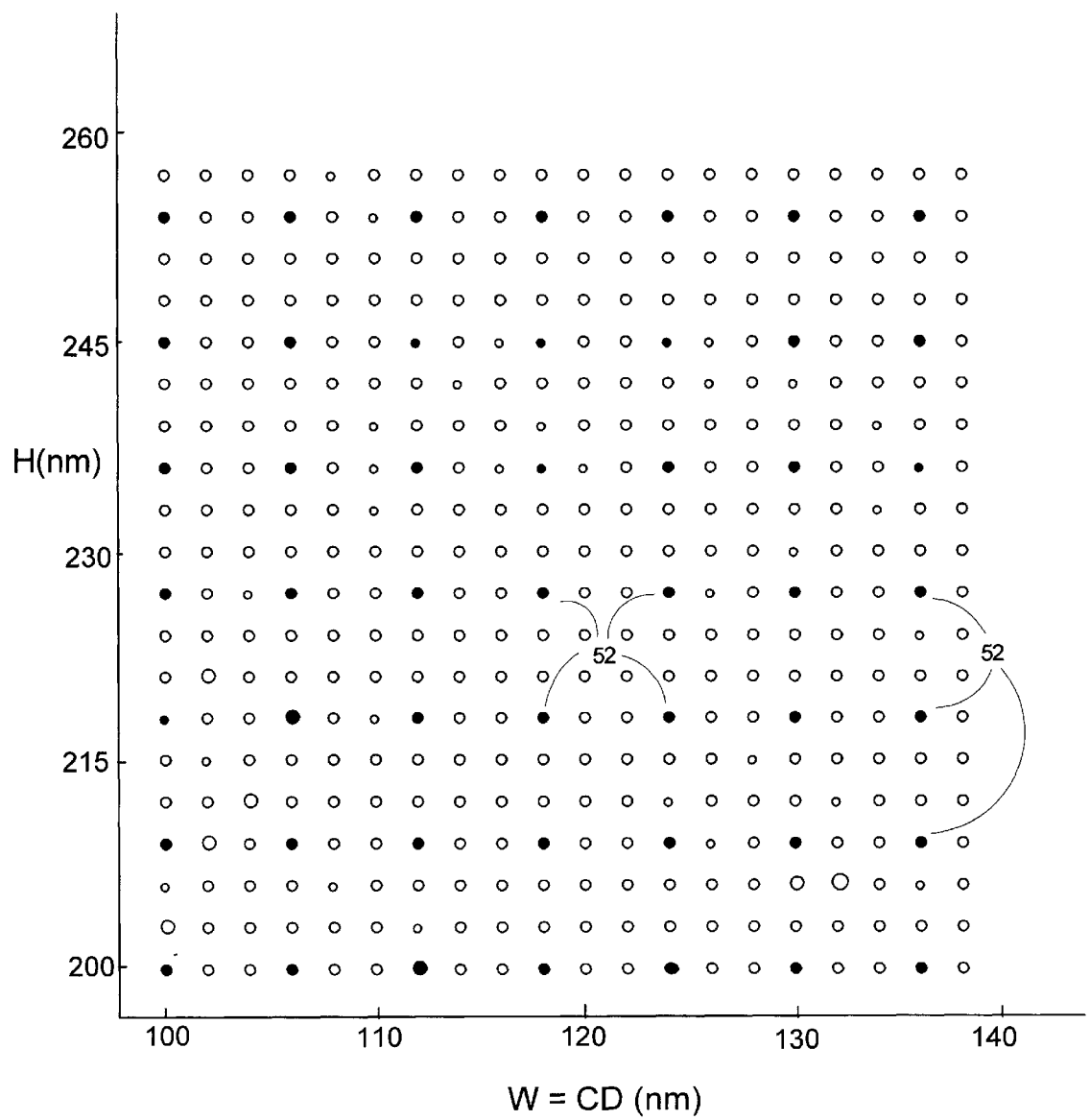
FIG. 5 illustrates a grid of profile parameter values and indicates sampling points for which a Jacobian matrix is calculated.

In Step 480, using the grating response simulator, calculate the matrix elements of J for several grid points corresponding to different values of the structural parameters for the sample structure. For example, if a polysilicon step of height H and bottom width W, as in FIG. 2, is being measured, matrix elements of J for several J-matrices corresponding to points in a grid composed of a range of values of H and W are calculated. The grid points correspond to values of H and W for which a simulated library diffraction spectrum has been calculated. An example is illustrated in FIG. 5. In this case the range of W is between 100 to 140 nm, and library simulated diffraction spectra have been calculated for W values at 2 nm spacing, and the range of H is between 200 to 260 nm with library simulated diffraction spectra calculated for H values at 3 nm spacing. In this example the J matrix elements are calculated for every third grid point in each dimension, wherein matrix elements of J matrices corresponding to grid points 52 are calculated. This sampling of only a portion of the grid points significantly reduces the calculation time, but requires the approximation that the J matrix is substantially the same in a small area of the grid.

The method of calculating the matrix elements of J is similar to the method of calculating the response of the diffraction spectrum to small metrology hardware parameter variations in the first embodiment described herein. Each partial derivative in the J matrix is approximated by varying a parameter, $K_0$ by way of example, a small amount called $\Delta K_0$, then calculating $\Delta S_i$, the change in the spectral scattering response function $S(\lambda_i)$ due to the change in $K_0$. $\partial S_i/\partial K_0$ is approximated to be equal to $\Delta S_i/\Delta K_0$. The variation of the parameters must be small enough so that the linear response relation is an accurate approximation. Determination of the maximum parameter variation to satisfy the linearity requirement to a specified extent can be performed using the methods described in the aforementioned co-pending U.S. Patent Application by Junwei Bao, et al., entitled *"Profile Refinement for Integrated Circuit Metrology"*.

In Step 490, subtract from each component of the actual parameter vector V the corresponding component of the ideal parameter vector $V_0$ used in the formation of the library of diffraction spectra. By way of example, if the parameter vector V were that of the example of Step 400, the subtraction would be of the form $$\Delta V=V-V_0=(AOI-AOI_0, NA-NA_0, K_0-K_{00}, K_2-K_{20})$$

where $\Delta V$ is termed the parameter modification vector.

In Step 500, calculate a spectral scattering response modification ΔS by matrix multiplication of the Jacobian matrix J by the parameter modification vector ΔV:

$$\Delta S = J \cdot \Delta V$$

where ΔS is a vector with the same number of components as S, usually 50.

The spectral scattering response modification for any library profile is determined using the calculated J matrix at the grid point closest to that of the library profile; e.g., in the example of step 480, in order to modify the library spectrum for a profile with W=128 nm and H=254 nm, the J matrix calculated at W=126 nm and H=257 nm would be used.

The J matrix elements can be calculated for each of the building block process structures and stored in a database. The J matrix elements can be calculated corresponding to the likely parameters, which might be variable, for example, using more than two K's to match the actual n vs λ curve to the ideal curve. Then in a real situation, the subset of those elements, which are to be included are determined, and the extraneous matrix elements corresponding to the parameters not included are set to zero, thereby having no effect on ΔS. Alternatively, the Δp's of extraneous parameters can be set to zero in the ΔV vector. Either of these approaches allows for a simple transformation between various pieces of metrology hardware and material batches; only the parameter modification vector will need to be determined and the matrix multiplication performed.

In a sub-embodiment, the database can be expanded to include a library of J matrix elements encompassing a spectrum of values for each metrology hardware and material parameter across the likely ranges for the pieces of applicable equipment and different material batches.

In Step 520, form a modified spectral scattering response function S' wherein $$S' = S + \Delta S,$$

where each component of S' is the direct sum of the corresponding components of S and ΔS.

This modified spectral scattering response function S' is the modified version of the library diffraction spectrum, i.e., spectral scattering response function S, which has been customized to the parameters corresponding to the particular piece of metrology hardware and material batches being used.

In Step 540, create a modified library of diffraction spectra to be used with the particular piece of metrology hardware for profiling samples made from the particular material batch.

The expanded database of the sub-embodiment described in Step 500 may also include modified library diffraction spectra according to each data point (corresponding to a particular parameter vector). The density of data points necessary to ensure linearity of response between data points can be determined according to the methods described in the aforementioned co-pending U.S. Patent Application by Jun-wei Bao, et al., entitled "*Profile Refinement for Integrated Circuit Metrology*". According to this sub-embodiment, the actual parameters of a system in use are determined, then the actual parameter vector is input to a querying device which accesses the database and outputs the modified library diffraction spectra. FIG. 3b shows a possible configuration of such a system.

Figure 6:
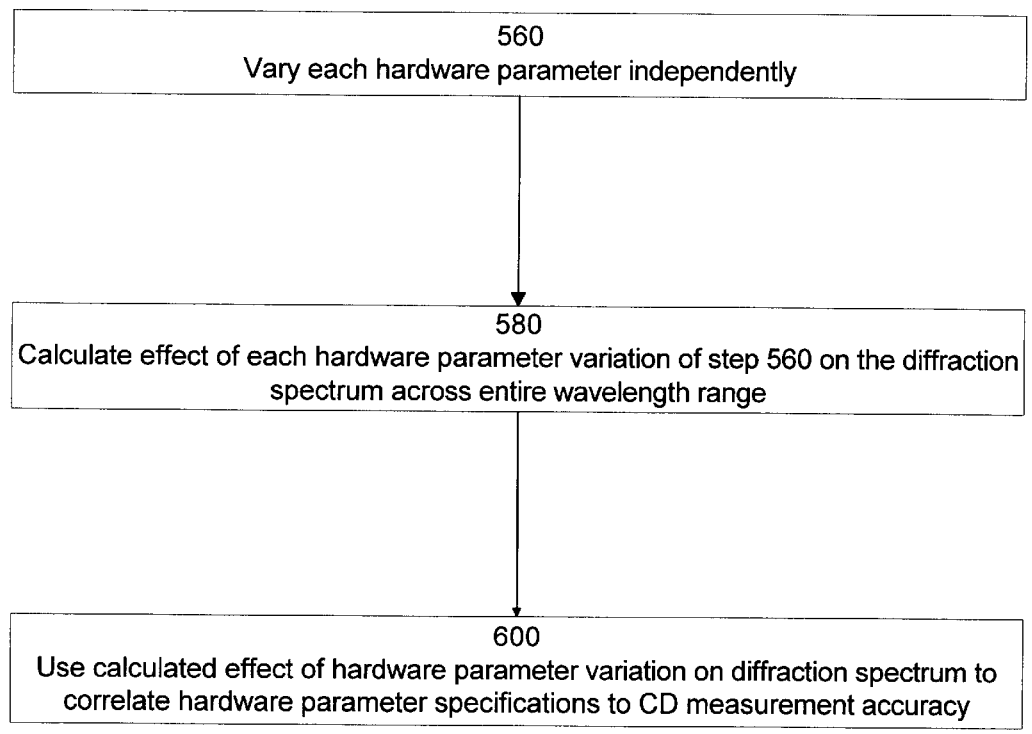
FIG. 6 is a summary flow chart illustrating a first embodiment of the invention.

The method illustrated by the two embodiments disclosed herein includes modifying a diffraction spectrum according to small input parameter changes. In the first embodiment, each parameter (corresponding to a metrology hardware specification parameter) is varied independently (Step 560), and the effect of the parameter variation on the diffraction spectrum across the entire wavelength range is calculated (Step 580). This inventive method, which utilizes comparison of measured CD's corresponding to the parameter variations, provides the capability of correlating metrology hardware parameter specifications to desired CD measurement accuracy (Step 600). FIG. 6 is a summary flow chart illustrating this embodiment.

Figure 7:
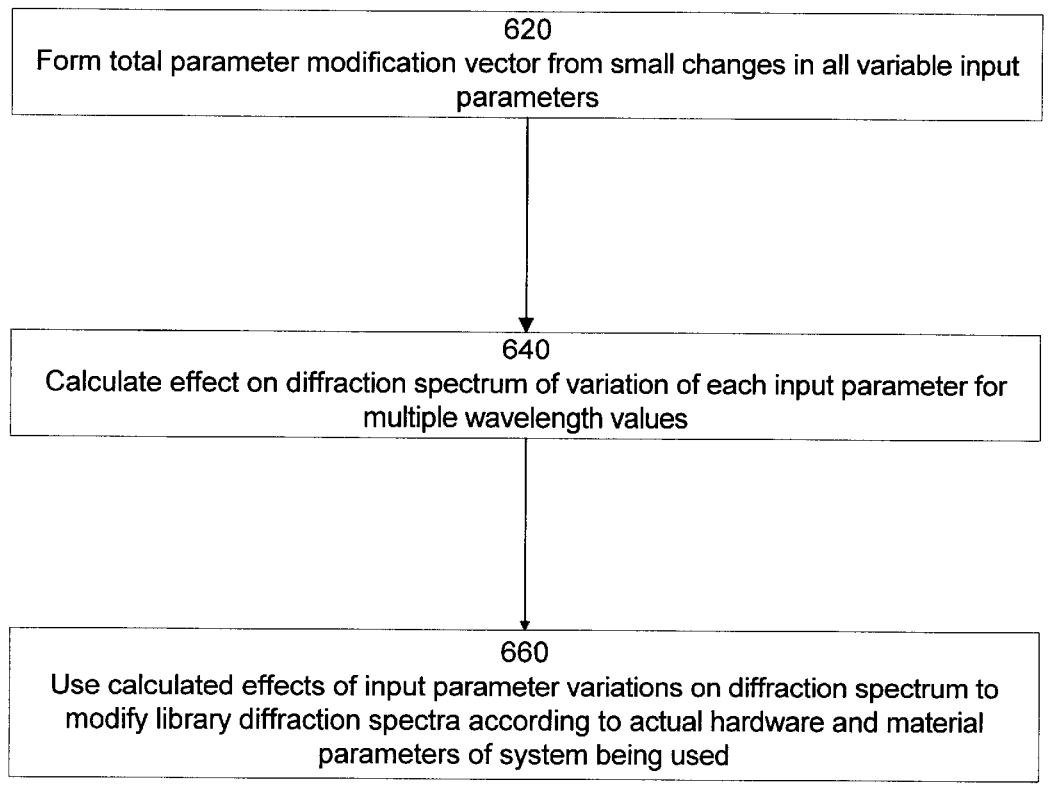
FIG. 7 is a summary flow chart illustrating a second embodiment of the invention.

In the second embodiment, the small input parameter changes are considered as a total parameter modification vector (Step 620), and the effect of the parameter variation on the diffraction spectrum is calculated for each input parameter for each of a large number of wavelength values across the wavelength range (Step 640). This enables modification of the library diffraction spectrum according to the actual parameters of the particular 1) metrology hardware and 2) material batch used (Step 660). FIG. 7 is a summary flow chart illustrating this embodiment. Both embodiments assume linear response between the amount of parameter variation and the effect of its variation, over the small range of parameter variation considered.

It is not intended that the invention be restricted to the exact embodiments described herein. It is clear to one skilled in the art that modifications to the exact method can be made without departing from the inventive concept. For example, n and k may be used as input parameters in the second embodiment, rather than $K_0$ and $K_2$. The method may be used not only to calibrate the library spectra between different pieces of metrology hardware, but also to calibrate the library spectra over time for a single piece of metrology hardware, to compensate for wear-induced drifting of metrology hardware parameters. The method can also be applied to other kinds of metrology than optical metrology, such as electron metrology (e.g., CD SEM, TEM), electrical metrology (e.g., capacitor), or mechanical metrology (e.g., AFM). The scope of the invention should be construed in view of the claims.

We claim:

1. A method in integrated circuit metrology for adapting a library of metrology signals for use with different metrology systems, each of the metrology systems comprising a metrology hardware device with associated metrology hardware device parameters and a sample including a sample material with associated material parameters, the method comprising:

specifying ranges for system parameters of a selected ideal metrology system, the system parameters comprising metrology hardware device parameters and material parameters;

verifying that a first metrology system has system parameters within the specified system parameter ranges of the ideal metrology system;

adapting a library of metrology signals functionally operative with the ideal metrology system to be functionally operative with tile first metrology system; and using the library of metrology signals to obtain profile data of integrated circuit structures;

wherein hardware device parameters include one or more of angle of metrology beam incidence, numerical aperture, wavelength range, polarization, and noise.

2. The method of claim 1 wherein the step of verifying that the first metrology system has system parameters within specified system parameter ranges of an ideal metrology system comprises:

determining a maximum acceptable variation in measurements from the sample;

calculating maximum specification ranges of the metrology hardware device parameters corresponding to the maximum acceptable variation in measurements; and comparing specification ranges of the metrology hardware device parameter for the first metrology system with the calculated maximum specification ranges of the metrology hardware device parameter.

3. The method of claim 2, wherein the metrology system is an optical metrology system.

4. The method of claim 1, wherein the step of adapting the library of metrology signals to be functionally operative with the first metrology system comprises:

a) calculating a change in a first metrology signal from the library of metrology signals at multiple wavelength values as each of the system parameters is varied within a small range;

b) evaluating the ratio between the variation in each of the system parameters and the change in the first metrology signal at the multiple wavelength values;

c) determining the variation between actual system parameters of the first metrology system and corresponding ideal system parameters of the ideal metrology system; and d) calculating a revised first metrology signal corresponding to the ratios of steps a) and b) and the variation between the actual system parameters and the ideal system parameters.

5. The method of claim 4, wherein the metrology system is an optical metrology system.

6. A method of revising a library of simulated metrology signals calculated using ideal system parameters of an ideal metrology system, so as to be optimized to actual system parameters for a first metrology system including a first metrology hardware device and a first sample material, the system parameters comprising metrology hardware device parameters and material parameters, comprising:

a) calculating the change in a first simulated metrology signal S at each of multiple wavelength values as each of the system parameters is varied;

b) evaluating the ratio between the variation in each of the system parameters and the change in the first simulated metrology signal at each of the multiple wavelength values;

c) determining the actual system parameters for the first metrology system;

d) determining the variation between the actual systems parameters and corresponding ideal system parameters;

e) calculating a revised first simulated metrology signal corresponding to the ratios of steps a) and b) and the variation between the actual systems parameters and the ideal system parameters; and f) repeating steps a)–e) for instances of simulated metrology signals from the library.

7. The method of claim 6, wherein the ideal metrology system and the first metrology system are optical metrology systems.

8. The method of claim 6, further including the step of assuming a linear relation between each small variation of the system parameters and its associated change in the simulated metrology signal.

9. The method of claim 6, wherein the metrology signals are diffraction spectra, and wherein the library is a refined resolution library, the refined resolution library created with a density of library data points necessary in order to ensure a specified maximum extent of non-linearity between the library data points.

10. The method of claim 9, wherein the diffraction spectra are calculated by a grating response simulator, and wherein the system parameters an inputs to the grating response simulator.

11. The method of claim 10, wherein the step of calculating the revised first diffraction spectrum S corresponding to the ratios of step b) and the variation between the actual systems parameters and the ideal system parameters comprises:

forming a parameter modification vector $\Delta V$ having components $\Delta p_j$ wherein $\Delta p_j$ is the variation between th actual value and the ideal value of the $j^{th}$ system parameter;

forming a matrix J having matrix elements $J_{ij}=\Delta S_i/\Delta p_j$ wherein $\Delta S_i$ equals the change in the diffraction spectrum due to $\Delta p_j$ at an $i^{th}$ wavelength value;

calculating a spectral scattering response modification $\Delta S$ according to mar multiplication $\Delta S=J*\Delta V$; and forming a revised first diffraction spectrum S' according to $S'=S+\Delta A$.

12. The method of claim 11, wherein the ideal metrology system and the first metrology system are optical metrology systems.

13. The method of claim 10, wherein the calculation of the diffraction spectra is done using Rigorous Coupled-Wave Analysis (RCWA).

14. The method of claim 6, wherein the metrology hardware device parameters include angle of incidence of beam onto the sample, numerical aperture, polarization, and/or azimuthal angle of incidence with respect to the grating direction, and wherein the material parameters include n, k, parametric constants in equations for n and k, and/or sample surface roughness.

15. The met of claim 6, wherein the actual material parameters are determined by:

measuring material properties and comparing the measured material properties with associated ideal material properties used in calculating the library diffraction spectra; and calculating modifications to the ideal material parameters required to match the ideal material properties to the associated measured material properties.

16. The method of claim 15, wherein the material property is index of refraction n; wherein the step of measuring material properties and comparing the measured material properties with associated ideal material properties comprises:

a) measuring n versus wavelength $\lambda$ across the wavelength range used in optical metrology measurements, for the batch of material to be profiled, to yield a measured n versus $\lambda$ curve; and b) providing an ideal n versus $\lambda$ curve for the material, and expressing the ideal n versus $\lambda$ curve as a parametric equation including a plurality of ideal parametric constants $K_{n0}$ for the index of refraction of the material;

wherein the step of calculating modifications to the ideal material parameters required to match the ideal material properties to the associated measured material properties comprises modifying the fewest possible number of the ideal parametric constants so as to match the ideal n versus $\lambda$ curve to the measured n versus $\lambda$ curve to a user-determined degree of matching; and wherein the modified parametric constants are included in the actual material parameters.

17. The method of claim 16, wherein the parametric equation is a Cauchy equation of the form $n_0(\lambda)=K_{00}+K_{20}/\lambda^2+K_{40}/\lambda^4$ where $K_{00}$ . . . are ideal parametric constants for the index of refraction of the material.

18. An integrated circuit metrology system comprising:
a metrology device comprising:
   a metrology beam source, the metrology beam source configured to direct a metrology beam at the integrated circuit structure, the integrated circuit structure having material parameters; and
   a beam receiver configured to receive and measure a metrology signal from the integrated circuit structure;
   a metrology profiler configured to compare metrology signal data from the metrology beam with profile data from a library of metrology signals, the library of metrology signals corresponding to an ideal metrology system having system parameters; and
   a metrology system adapter configured to adapt metrology data to be functionally operative with a plurality of metrology devices;
   wherein the metrology device, having system parameters including metrology hardware device parameters and material parameter is configured to have the system parameters within specified system parameter ranges of the system parameters of the ideal metrology system; and
   wherein the metrology profiler is configured to adapt the library of metrology signals to be functionally operative with the metrology device.

19. The system of claim 18, wherein the metrology system adapter is configured to:
   determine a maximum acceptable variation in measurements from the integrated circuit structurealculate maximum specification ranges of the metrology hardware device parameters corresponding to the maximum acceptable variation in measurements; and
   verify that the metrology device has metrology hardware device parameters within the maximum specification ranges.

20. The system of claim 18, wherein the metrology system adapter is configured further to:
   a) calculate change in a first metrology signal from the library at multiple wavelength values as each of the system parameters is varied within a small range;
   b) evaluate the ratio between the variation in each of the system parameters and the change in the first metrology signal at the multiple wavelength values;
   c) determine the variation between actual first system parameters of the first metrology system and corresponding system parameters of the ideal metrology system;
   d) calculate a revised first metrology signal corresponding to the ratios of steps a) and b) and the variation between the actual first system parameters and the system parameters of the ideal metrology system; and
   e) repeat steps a)–d) or instances of metrology signals from the library.

21. A computer-readable storage medium containing computer executable code to adapt a library of metrology signals, the library of metrology signals corresponding to an ideal metrology system having system parameters, to be functionally operative with a first metrology system having actual system parameters by instructing a computer to operate as follows:
   a) calculating the change in a first metrology signal from the library at multiple wavelength values as each of the system parameters is varied within a small range;
   b) evaluating the ratio between the variation in each of the system parameters and the change in the first metrology signal at the multiple wavelength values;
   c) determining the variation between actual system parameters of the first metrology system and corresponding system parameters of an ideal metrology system;
   d) calculating a revised first metrology signal corresponding to the ratios of steps a) and b) and the variation between the actual system parameters and the system parameters of the ideal metrology system; and
   e) repeating steps a)–d) for instances of metrology signals from the library.

22. The computer-readable storage medium of claim 21, further containing computer executable code to determine the profile of an integrated circuit structure from a measured metrology signal by instructing a computer to operate as follows:
   comparing the measured metrology signal with instances of revised metrology signals from the library; and
   selecting a best match revised library metrology signal to the measured metrology signal.

23. A computer-readable storage medium containing stored data including a set of first simulated diffraction spectra corresponding to a set of first grating profiles measured by a first metrology system, and a set of second simulated diffraction spectra corresponding to the set of first grating profiles, the set of second simulated diffraction spectra being a modification of the set of first simulated diffraction spectra optimized to an actual system parameter vector of a second metrology system.

24. The computer-readable storage medium of claim 23, wherein the set of first simulated diffraction spectra, the set of second simulated diffraction spectra, and the actual system parameters comprise a database associating the actual system parameter vector of the second metrology system with the modification of the set of first simulated diffraction spectra optimized to the actual system parameter vector of the second metrology system.

25. The computer-readable storage medium of claim 24, wherein the database is accessible by a querying device.

26. A system specification server including the computer-readable storage medium of claim 25.

27. A system specification system for coupling to an integrated circuit fabrication system, the system specification system including:
   the system specification server of claim 26,
   a querying device adapted to input an actual system parameter vector into the system specification server and to receive an output of the modification of the set of first simulated diffraction spectra optimized to the actual system parameter vector; and
   means for coupling the system specification system to the integrated circuit fabrication system.

* * * * *